(12) United States Patent
Martinez et al.

(10) Patent No.: US 7,914,588 B2
(45) Date of Patent: Mar. 29, 2011

(54) SYNTHESIS OF FLUORESCENT METAL NANOCLUSTERS

(75) Inventors: Jennifer S. Martinez, Santa Fe, NM (US); R. Brian Dyer, Los Alamos, NM (US); Dung M. Vu, Los Alamos, NM (US); Yuping Bao, Tuscaloosa, AL (US); Chang Zhong, Stanford, CA (US)

(73) Assignee: Los Alamos National Security, LLC, Los Alamos, NM (US)

( * ) Notice: Subject to any disclaimer, the term of this patent is extended or adjusted under 35 U.S.C. 154(b) by 997 days.

(21) Appl. No.: 11/786,190

(22) Filed: Apr. 10, 2007

(65) Prior Publication Data

US 2010/0009427 A1  Jan. 14, 2010

(51) Int. Cl.
C07F 1/10 (2006.01)
C07F 1/12 (2006.01)
A61K 33/00 (2006.01)

(52) U.S. Cl. ........ 977/731; 977/810; 556/110; 424/9.34
(58) Field of Classification Search .................. None
See application file for complete search history.

(56) References Cited

U.S. PATENT DOCUMENTS

| | | | |
|---|---|---|---|
| 4,507,466 | A | 3/1985 | Tomalia et al. |
| 5,560,929 | A | 10/1996 | Hedstrand et al. |
| 5,631,329 | A | 5/1997 | Yin et al. |
| 6,664,315 | B2 | 12/2003 | Tomalia et al. |
| 6,995,234 | B2 | 2/2006 | Tomalia et al. |
| 2002/0045714 | A1 | 4/2002 | Tomalia et al. |
| 2003/0109056 | A1 | 6/2003 | Vossmeyer et al. |
| 2004/0028694 | A1 | 2/2004 | Young et al. |
| 2006/0051878 | A1 | 3/2006 | Dickson et al. |
| 2006/0148104 | A1 | 7/2006 | Marini et al. |

FOREIGN PATENT DOCUMENTS

WO  PCT/US05/007649  3/2004

OTHER PUBLICATIONS

Faraday, "The Bakerian Lecture: Experimental Relations of Gold (and Other Metals) to Light," Philosophical Transactions of the Royal Society of London, vol. 147, 1857, pp. 145-181.
Tomalia et al., "A New Class of Polymers: Starburst-Dendritic Macromolecules," Polymer Journal, vol. 17, 1985, No. 1, pp. 117-132.
Polaskova et al., "Synthesis of Nanotubule-Forming Cyclic Octapeptides via an Fmoc Strategy," Aust. J. Chem., vol. 51, 1998, pp. 535-540.
Wilcoxon et al., "Photoluminescence from Nanosize Gold Clusters," J. of Chem. Phy., vol. 108, No. 21, Jun. 1998, pp. 9137-9143.
Balogh et al., "Poly(Amidoamine) Dendrimer-Templated Nanocomposites. 1. Synthesis of Zerovalent Copper Nanoclusters." J. Am. Chem. Soc., vol. 120, No. 29, Jul. 1998, pp. 7355-7356.
Garcia et al., "Preparation and Characterization of Dendrimer-Gold Colloid Nanocomposites," Anal. Chem., vol. 71, No. 1, Jan. 1999, pp. 256-258.
Bigioni et al., "Near-Infrared Luminescence from Small Gold Nanocrystals," J. Phys. Chem. B, vol. 104, No. 30, Aug. 2000, pp. 6983-6986.
Varnavski et al., "Ultrafast Time-Resolved Photoluminescense From Novel Metal-Dendrimer Nanocomposites," J. Chem. Phys., vol. 114, No. 5, Feb. 2001, pp. 1962-1965.
Peyser et al., "Photoactivated Fluorescence from Individual Silver Nanoclusters," Science, vol. 291, Jan. 2001, pp. 103-106.
Link et al, "Visible to Infrared Luminescence from a 28-Atom Gold Cluster," J. Phys. Chem. B, vol. 106, No. 13, Apr. 2002, pp. 3410-3415.
Shi et al., "Convenient Synthesis of Human Calcitonin and Its Methionine Sulfoxide Derivative," Bioorg. Med. Chem. Lett., vol. 12, Aug. 2002, pp. 2237-2240.
Hedden et al., "Structure and Dimensions of PAMAM/PEG Dendrimer-Star Polymers," Macromolecules, vol. 36, No. 6, Mar. 2003, pp. 1829-1835.
Zheng et al., "High Quantum Yield Blue Emission from Water-Soluble $Au_8$ Nanodots," J. Am. Chem. Soc., vol. 125, No. 26, Jul. 2003, pp. 7780-7781.
Lee et al., "Electrochemistry and Optical Absorbance and Luminescence of Molecule-like $Au_{38}$ Nanoparticles," J. Am. Chem. Soc., vol. 126, No. 19, May 2004, pp. 6193-6199.
Lee et al., "Strong Blue Photoluminescence and ECL from OH-Terminated PAMAM Dendrimers in the Absence of Gold Nanoparticles," J. Am. Chem. Soc., vol. 126, No. 27, Jul. 2004, pp. 8358-8359.
Wang et al., "Fluorescence Emission From Dendrimers and Its pHDependence," J. Am. Chem. Soc., vol. 126, No. 41, Oct. 2004,pp. 13204-13205.
Petty et al., "DNA-Templated Ag Nanocluster Formation," J. Am Chem. Soc., vol. 126, No. 16, Apr. 2004, pp. 5207-5212.
Zheng et al., "Highly Fluorescent, Water-Soluble, Size-Tunable Gold Quantum Dots," Amer. Phys. Soc., vol. 93, No. 7, Aug. 2004, pp. 077402-1-077402-4.
Tran et al., "Synthesis and Spectroscopic Observation of Dendrimer-Encapsulated Gold Nanoclusters," Chem. Commun., 2006, pp. 2400-2401.

*Primary Examiner* — Anand U Desai
(74) *Attorney, Agent, or Firm* — Samuel L. Borkowsky

(57) ABSTRACT

Fluorescent metal nanoclusters were prepared.

20 Claims, No Drawings

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1
```

-continued

```
Cys Cys Cys Cys Gly Ser Ser Arg Asp Glu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Pro His Asp Ala Arg Gly Arg Ser Ala Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Ser Asp Ser Tyr Ile His Ala Arg Pro Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Pro Leu Val Glu Arg Leu Tyr Pro Arg Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Thr Gly Arg Asp Thr Lys Thr Gly Thr Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Arg Pro Thr Asn Ala Gly Lys Met Thr Asn
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Val Ala Pro Trp Pro Pro Leu Thr Arg Lys
1               5                   10
```

```
<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Met Ala Pro Thr Pro Pro Leu Thr Arg Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Arg Trp Ala Pro Met Ser Cys Leu Val Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Tyr Leu Glu Phe Pro Arg Arg Gly Tyr Leu Leu Pro
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic Construct

<400> SEQUENCE: 11

Ala Ser Ser Pro His Asp Ala Arg Gly Arg Ser Ala Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Construct

<400> SEQUENCE: 12

Ala Ser Ser Ser Asp Ser Tyr Ile His Ala Arg Pro Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic Construct

<400> SEQUENCE: 13

Ala Ser Ser Pro Leu Val Glu Arg Leu Tyr Pro Arg Leu
1               5                   10
```

```
<210> SEQ ID NO 14
<211> LENGTH: 13
<212> TYPE: PRT
<213> ORGANISM: Artificial Sequence
<220> FEATURE:
<223> OTHER INFORMATION: Synthetic Construct

<400> SEQUENCE: 14

Ala Ser Ser Thr Gly Arg Asp Thr Lys Thr Gly Thr Ser
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Ala Ser Ser Arg Pro Thr Asn Ala Gly Lys Met Thr Asn
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic Construct

<400> SEQUENCE: 16

Ala Ser Ser Val Ala Pro Trp Pro Pro Leu Thr Arg Lys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct

<400> SEQUENCE: 17

Ala Ser Ser Met Ala Pro Thr Pro Pro Leu Thr Arg Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Ala Ser Ser Arg Trp Ala Pro Met Ser Cys Leu Val Thr
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Ala Ser Ser Tyr Leu Glu Phe Pro Arg Arg Gly Tyr Leu Leu Pro
1               5                   10                  15

<210> SEQ ID NO 20
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 20

Pro Gly Val Arg Leu Tyr Pro Met Arg Leu
1               5                   10
```

US 7,914,588 B2

SYNTHESIS OF FLUORESCENT METAL NANOCLUSTERS

STATEMENT REGARDING FEDERAL RIGHTS

This invention was made with government support under Contract No. DE-AC51-06NA25396 awarded by the U.S. Department of Energy. The government has certain rights in the invention.

FIELD OF THE INVENTION

The present invention relates generally to nanoclusters and more particularly to the preparation of fluorescent metal nanoclusters using templates such as dendrimers, polypeptides, proteins, and small molecules.

BACKGROUND OF THE INVENTION

The synthesis of metal particles referred to herein as nanoclusters or nanoparticles has been the subject of considerable interest. Small size may be needed for effective catalysts and is usually needed for high-resolution labeling of biological samples for transmission electron microscopic (TEM) examination. Small size is also expected to be important for fluorescent tags useful for labeling non-fluorescent biomolecules (proteins, nucleic acids, for example) and their assemblies that are not naturally fluorescent. Fluorescent tags can be so large that they perturb biomolecules as the biomolecules interact with a binding partner, and tags might bleach rapidly, which can limit the time window that a molecular event for a biomolecule can be measured. Fluorescent noble metal nanoclusters (gold or silver, for example) might be better tags than those currently available because fluorescent noble metal nanoclusters can exhibit a strong, size-dependent light emission, can be very small, and can be attached to biomolecules.

Dendrimers, known also as dense star polymers, have been used as templates to prepare large non-fluorescent metal nanoclusters and nanoparticles.

Oligonucleotides, proteins, and DNA have been reported as templates to prepare fluorescent metal nanoclusters.

SUMMARY OF THE INVENTION

In accordance with the purposes of the present invention, as embodied and broadly described herein, the present invention includes a method for preparing fluorescent nanoclusters. The method includes mixing an aqueous solution of a template and a metal precursor at a temperature that prevents the substantial formation of non-fluorescent metal nanoclusters and nanoparticles but allows the formation of a complex between the template and metal from the metal precursor, whereby a complex forms between the template and metal from the metal precursor; and increasing the temperature, whereby the complex is reduced and fluorescent metal nanoclusters are produced.

The invention is also concerned with a method for preparing fluorescent metal nanoclusters that includes mixing a solution of a metal precursor and a polypeptide at a temperature and for an amount of time sufficient to convert at least some of the metal precursor to fluorescent metal nanoclusters.

The invention is also concerned with a method of preparing fluorescent metal nanoclusters that includes mixing a two-phase liquid system having an aqueous phase and an organic phase, wherein a biocompatible reducing agent and a template are in the aqueous phase, and wherein a metal precursor chosen from gold and silver is in the organic phase. The template is chosen from dendrimers, polypeptides, and proteins. After mixing the two-phase system, the aqueous phase is separated from the organic phase and the aqueous phase is heated.

DETAILED DESCRIPTION

The invention is concerned with the preparation of fluorescent metal nanoclusters using a template such as a dendrimer, a polypeptide, a protein, or a small molecule. If desired, the fluorescent metal nanoclusters can be separated from the template and attached to a biomolecule.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art.

Metal nanoclusters are defined as metal particles having a size equal to or less than 10 nanometers (nm). In some embodiments, fluorescent nanoclusters prepared according to this invention have a size of equal to or less than one nanometer. Metal nanoparticles are larger than metal nanoclusters. Metal nanoparticles are defined herein as metal particles having a size greater than 10 nm and less than 1000 nm. The invention is not concerned with preparing metal nanoparticles, or with preparing metal nanoclusters that are not fluorescent.

In some embodiments, the preparation of fluorescent metal nanoclusters involves using single-phase systems of metal precursor and template where the phase can be an aqueous phase or an organic phase. In other embodiments, a two-phase system that includes both an aqueous phase and an organic phase is used to prepare fluorescent metal nanoclusters.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid (i.e. peptoid).

Amino acids may be referred to herein by either their commonly known three letter symbols or by the one-letter symbols recommended by the IUPAC-IUB Biochemical Nomenclature Commission. Some amino acids and their one letter symbols include Alanine (A), Glycine (G), Aspartic acid (D), Glutamic acid (E), Asparagine (N), Glutamine (Q), Arginine (R), Lysine (K), Isoleucine (I), Leucine (L), Methionine (M), Valine (V), Phenylalanine (F), Tyrosine (Y), Tryptophan (W) Serine (S), Threonine (T), Cysteine (C), and Methionine (M).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three-dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three-dimensional structure of a polypeptide monomer. "Quaternary structure" refers to the three dimensional structure formed by the noncovalent association of independent tertiary units. Some embodiment polypeptides of the invention have a chain structure. Others have a ring structure. Still others have both a chain portion and a ring portion.

In an some embodiments, fluorescent metal nanoclusters are synthesized using a poly(amidoamine) (PAMAM) dendrimer as a template. It should be understood that PAMAM dendrimer is meant to include any generation (G) of dendrimer, for example, a 0.5 generation (G0.5) dendrimer, a $1^{st}$ generation (G1) dendrimer, a 1.5 generation (G1.5) dendrimer, a $2^{nd}$ generation (G2) dendrimer, a 2.5 generation G2.5) dendrimer, a $3^{rd}$ generation (G3) dendrimer, a 3.5 generation (G3.5) dendrimer, a $4^{th}$ generation (G4) dendrimer, a 4.5 generation (G4.5) dendrimer, a $5^{th}$ generation (G5) dendrimer, a 5.5 generation (G5.5) dendrimer, a $6^{th}$ generation (G6) dendrimer, and so forth up to and including a $20^{th}$ generation (G20) dendrimer and all generations in between.

It should also be understood that embodiment dendrimers are not limited to any particular core. For example, dendrimers useful with the invention may have an amine core, an ethylenediamine core, etc.

It should also be understood that embodiment dendrimers such as, but not limited to, poly(amidoamine) and poly(amidoethylenediamine), DAB-Am-16, polypropylenimine hexadecaamine dendrimer, or cyclotriphosphazene-PMMH-24 dendrimer, may include those modified with terminal functional groups such as hydroxyl (OH) and carboxyl (COOH).

In some embodiments for making fluorescent nanoclusters that involve the use of a dendrimer, a solution of noble metal precursor and dendrimer is prepared and the metal precursor and dendrimer are allowed to react in the dark at a cold temperature to form a complex. After the complex forms, the solution is allowed to warm. Sometimes, the solution is heated after the metal-dendrimer complex forms. As the metal-dendrimer complex forms, it should be understood that the temperature of the solution should be cold enough to prevent, or at least minimize, the formation of nanoparticles but not cold enough to prevent the formation of the complex. While a temperature of 4 degrees Celsius was found to be cold enough to prevent or at least minimize formation of nanoparticles, but not cold enough to prevent the formation of the complex, it should be understood that any temperature cold enough for complex formation while preventing or at least minimizing the formation of nanoparticles is within the scope of this invention. In many embodiments involving the use of a dendrimer, the cold solution of metal precursor and dendrimer is kept in the dark because it is believed that darkness plays a role in preventing the formation of nanoparticles. Some non-limiting examples of situations for keeping the solution in the dark include keeping the solution in a room with the lights out and blinds pulled over windows, or when the solution is shielded from room light and ambient light coming from outside the room.

The nanoclusters can be separated from the template. In a non-limiting embodiment, gold nanoclusters formed using a dendrimer template can be separated from the template using an alkanethiol. In another embodiment, gold nanoclusters are separated from a dendrimer by adjusting the pH of the solution to a pH of, for example, pH 2-3. At this pH, the nanoclusters can escape from the dendrimer.

After separating nanoclusters from the template, they can be attached to a biomolecule. Attachment might be in the form of a chemical bond, or just in the form of a close association with the biomolecule. In an embodiment, after exposing a nanocluster-template to conditions where the nanoclusters escape from the template, the nanoclusters can be further separated using a membrane. The result is a solution of nanoclusters that does not include the template (a dendrimer, for example). The dendrimer-free solution of nanoclusters is then mixed with a biomolecule (an aqueous solution of a cysteine-rich polypeptide, for example). It should be understood that the invention should not be limited to any particular procedure for separating the nanoclusters from the template, or for attaching them to a biomolecule.

In some embodiments, a biocompatible reducing agent is added to a solution of noble metal precursor and template (a dendrimer, polypeptide, protein, small molecule, for example). Some non-limiting examples of biocompatible reducing agents are sugars, Chitosan, and ascorbic acid. The addition of the reducing agent is sometimes needed when conditions otherwise will not promote a chemical reduction that produces fluorescent nanoclusters. Sometimes, the addition of the biocompatible reducing agent speeds up a chemical reduction. Sometimes, the addition of the reducing agent results in a mixture of fluorescent nanoclusters. In at least some cases where a reducing agent is used to prepare a mixture of fluorescent gold nanoclusters, the relative concentrations of the nanocluster sizes can be adjusted by adjusting the amount of biocompatible reducing agent to the amount of dendrimer to the amount of gold precursor.

In some embodiments, the preparation of fluorescent nanoclusters results in monodisperse product that is largely a single type of nanocluster.

An aspect of the invention is concerned with polypeptides useful as templates for synthesizing metal nanoclusters, and with the synthesis of nanoclusters in an aqueous medium using the polypeptide templates. An embodiment polypeptide is the cysteine rich polypeptide of the formula CCCCGSS-RDE (SEQ ID NO: 1). This polypeptide was prepared by solid phase peptide synthesis using standard Fmoc chemistry, and then used to prepare gold nanoclusters.

In some embodiments, the polypeptide templates are cyclic molecules with a β-hairpin and a cage structure. An embodiment polypeptide includes two type II′ beta turns (NG, yP, pG, where lower case letters represent D-amino acids), which may produce a well-defined structure even before the two ends are covalently bonded to each other.

Polypeptide templates can be designed with a length and composition to provide nanoclusters of a chosen size.

An aspect of this invention is related to the synthesis of nanoclusters using polypeptide templates selected by "phage display". Phage display technology involves the use of filamentous (i.e. M13) or lytic (i.e. T7) phage to display recombinant proteins and peptides. It is a well-known method for selecting proteins and peptides with desired functions or improved characteristics from complex libraries. Phage display is widely used, for example, in the isolation of human antibodies through clonal selection of antibody fragments in prokaryotic host systems. Filamentous phage from the Ff group, including M13, fl and fd phage, are commonly used. For some embodiments of this invention, phage display was used to select polypeptides useful for forming noble metal nanoclusters. A non-limiting list of polypeptides displayed by the M13 phage that are useful for preparing noble metal nanoclusters include, but are not limited to, PHDARGRSAG (SEQ ID NO: 2), SDSYIHARPR (SEQ ID NO: 3), PLVERLYPRL (SEQ ID NO: 4), TGRDTKTGTS (SEQ ID NO: 5), RPTNAGKMTN (SEQ ID NO: 6), VAPWPPLTRK (SEQ ID NO: 7), MAPTPPLTRK (SEQ ID NO: 8), RWAPMSCLVT (SEQ ID NO: 9), YLEFPRRGYLLP (SEQ ID NO: 10), ASSPHDARGRSAG (SEQ ID NO: 11), ASSSDSYIHARPR (SEQ ID NO: 12), ASSPLVERLYPRL (SEQ ID NO: 13), ASSTGRDTKTGTS (SEQ ID NO: 14), ASSRPTNAGKMTN (SEQ ID NO: 15), ASSVAPWPPLTRK (SEQ ID NO: 16), ASSMAPTPPLTRK (SEQ ID NO: 17), ASSRWAPMSCLVT (SEQ ID NO: 18), and ASSYLEFPRRGYLLP (SEQ ID NO: 19).

The following EXAMPLES illustrate some non-limiting embodiments related to the preparation of nanoclusters and their properties. In the EXAMPLES, ascorbic acid was obtained from the ALDRICH CHEMICAL COMPANY. An aqueous solution (20 mM) of ascorbic acid was prepared and used in some of the EXAMPLES. The G4OH dendrimer and G3.5COOH dendrimer were obtained from the ALDRICH CHEMICAL COMPANY as a 10% by weight solution in methanol and used as received. $HAuCl_4$ was obtained from the ALDRICH CHEMICAL COMPANY as a 0.2% by weight aqueous solution and used as received. Nanopure water (18 MOhm) was used for preparing solutions.

EXAMPLE 1

Preparation of Monodisperse Fluorescent $Au_8$ Nanoclusters

This preparation involves the formation of a complex between gold and a fourth generation hydroxyl-terminated poly(amidoethylenediamine) (G4OH) dendrimer. Four solutions were prepared. In each of the four solutions, the G4OH dendrimer (0.25 micromoles ($\mu$mol)) was added to nanopure water (5 milliliters (mL)), and then $HAuCl_4$ was mixed in. In one of the solutions, the gold to dendrimer ratio was 1:1. In another solution, the gold dendrimer ratio was 1:3. In the third solution, the gold dendrimer ratio was 1:12, and in the fourth solution, the gold to dendrimer ratio was 1:15. In each solution, gold ions formed a complex with the dendrimer after stirring the solution in the dark at a temperature of 4 degrees Celsius for 24 hours. Each solution was quickly prepared under ambient light and at temperature and then moved to a dark cold room (4 degrees Celsius). The solutions were then turned for three days at a temperature of about 37 degrees Celsius. Afterward, the solutions were examined using fluorescence spectrometry. The colorless solutions were subjected to light excitation at 387 nm. The light excitation produced fluorescence with a maximum emission at 458 nm. Based on a model known in the art as the Jellium model (see: Zheng et al., *Phys. Rev. Lett.*, vol. 93, (2004), pp. 077402-1, incorporated by reference), it was concluded that the fluorescence of the predominant nanocluster in the monodisperse product was due to $Au_8$. The solution having the 15:1 gold to dendrimer ratio had the highest fluorescence intensity and the fluorescence intensity decreased steadily as the gold to dendrimer ratio decreased, but the emission wavelength for all of the solutions was substantially the same. From these observations, it was concluded that the gold to dendrimer ratio affected the overall yield of nanoclusters, but not the nanocluster size. Additional experimental results suggest that the fluorescence did not arise from the G4OH dendrimer or from an oxidized byproduct of the G4OH dendrimer.

The gold nanoclusters can be separated from the dendrimer. This separation can be done using a variety of procedures including procedures known in the art. A non-limiting example for separating the gold nanoclusters from the dendrimer prepared according to this EXAMPLE, a two-phase system was prepared. The aqueous phase of the two-phase system was prepared by adding 1 mL gold nanoclusters prepared as described above in this EXAMPLE. The organic phase was prepared by adding dodecanethiol ($C_{12}H_{25}SH$, 10 $\mu$mol) in hexane (ALDRICH). The phases were stirred vigorously for a day at room temperature. Afterward, the clear organic phase was separated and measured by fluorescence spectrometry. A fluorescence emission similar to that in aqueous solution was detected, but with much lower emission intensity. While not wishing to be bound by the present explanation, the lower intensity is probably due to solvent quenching in the absence of dendrimer protection.

EXAMPLE 2

Preparation of Monodisperse Fluorescent $Au_{11}$ Nanoclusters

An aqueous solution of a gold precursor and a three and a half generation, carboxylic-terminated ethylenediamine core dendrimer (G3.5COOH) was prepared by adding G3.5COOH dendrimer (0.25 $\mu$mol) to nanopure water (5 mL), and then mixing in an amount of $HAuCl_4$ at a $HAuCl_4$ to dendrimer ratio of 1:15. The gold ions formed a complex with the dendrimer after stirring at 4 degrees Celsius in the dark for 24 hours. The appearance of a light brown color indicated that some of the gold precursor was reduced to gold nanoparticles. The brown component was removed by centrifugation at 13,000 rpm for 5 minutes. The supernatant solution did not display any fluorescence. A biocompatible reducing agent (ascorbic acid) was added (ratio of gold to ascorbic acid was 1:4) to the solution. After agitating the solution by turning it for three days at a temperature of about 37 degrees Celsius, the solution was examined by fluorescence spectrometry. Excitation of the colorless solution at 425 nanometers (nm) produced a green fluorescence with a maximum emission at 490 nm. No other emission maximum was observed. From these observations, in combination with the Jellium model for fluorescent nanoclusters, it was concluded that the fluorescent gold nanoclusters were monodisperse $Au_{11}$ nanoclusters. Additional experimental results suggest the fluorescence did not arise from the G3.5COOH dendrimer.

EXAMPLE 3

Preparation of Monodisperse Fluorescent $Au_8$ Nanoclusters Using a Two-Phase System A two-phase system was prepared. The aqueous phase of the two phase system was prepared by adding G4OH dendrimer (10 microliter (μL), 0.07 micromoles (μmol) to water H$_2$O (1 mL). The organic phase was prepared by adding AuPPh$_3$Cl (dendrimer/gold ratio 1/8) to toluene (0.2 mL). The phases were stirred vigorously for two days at room temperature. The clear aqueous phase was separated and transferred to a 2 mL glass vial. The vial was capped using a TEFLON-coated cap. The system was heated to 75 degrees Celsius with stirring for 48 hours. This preparation resulted in monodisperse Au$_8$ nanoclusters.

EXAMPLE 4

Preparation of a Mixture of Fluorescent Gold Nanoclusters Using Biocompatible Reducing Agent A solution of G4OH dendrimer (0.25 μmol) in nanopure water (5 mL) was prepared. HAuCl$_4$ was added to the solution. A gold-dendrimer complex formed after stirring the solution at 4 degrees Celsius in the dark for 24 hours. Ascorbic acid (20 mM) was added to the solution in a ratio of 4 parts ascorbic acid to one part gold. The solution was turned at a temperature of 37 degrees Celsius. The product was a clear, light yellow solution. The yellow color suggests that some of the gold was converted to larger nanoclusters. The solution was examined by fluorescence spectrometry. Fluorescence emission maxima of the solution suggests that the presence of gold nanoclusters of the formula Au$_8$, Au$_{13}$, Au$_{17}$, and Au$_{23}$. The predominant cluster size was Au$_{13}$, which has a maximum emission at 540 nm when excited at 450 nm.

EXAMPLE 5

Preparation of Fluorescent Gold Nanoclusters Using Buffered Solution

An aqueous solution was prepared at room temperature by adding ascorbic acid (20 μmol) to nanopure water (1 mL) and then adding HAuCl$_4$ at an ascorbic to gold ratio of 10:1. The solution was then incubated at 37 degrees Celsius for three days. The resulting colorless solution was examined by fluorescence spectrometry. The solution was excited at 362 nanometers and produced fluorescence at 432 nanometers. Additional experimental results suggest that the fluorescence did not arise from the buffer.

EXAMPLE 6

Preparation of Fluorescent Gold Nanoclusters Using Buffered Solution

An aqueous solution was prepared at room temperature by adding ascorbic acid (20 μmol) to tris(hydroxymethyl)aminomethane buffer (1 mL, 0.1 M, pH=8), and then adding HAuCl$_4$ at an ascorbic to gold ratio of 10:1. The solution was then incubated at 37 degrees Celsius for three days. The resulting colorless solution was examined by fluorescence spectrometry. The solution was excited at 315 nanometers and produced fluorescence at 385 nanometers. Additional experimental results suggest that the fluorescence did not arise from the buffer.

EXAMPLE 7

Preparation of a Mixture of Fluorescent Gold Nanoclusters Using Buffered Solution An aqueous solution was prepared at room temperature by adding ascorbic acid (20 μmol) to Phosphate Buffered Saline (PBS, 1 mL, 1 M, pH=7.2), and then adding HAuCl$_4$ at an ascorbic to gold ratio of 10:1. The solution was then incubated at 37 degrees Celsius for three days. The resulting colorless solution was examined by fluorescence spectrometry. The solution was excited at 370 nm and produced fluorescence at 450 nanometers that was due to the presence of gold nanoclusters. Additional experimental results suggest that the fluorescence did not arise from the buffer.

EXAMPLE 8

Preparation of Fluorescent Gold Nanoclusters Using Buffered Solution

An aqueous solution was prepared at room temperature by adding ascorbic acid (20 μmol) to HEPES (4-(2-hydroxyethyl)-1-piperazineethanesulfonic acid, 1 mL, 0.1 M pH=7.4), and then adding HAuCl$_4$ at an ascorbic to gold ratio of 10:1. The solution was then incubated at 37 degrees Celsius for three days. The resulting yellow solution with precipitates was examined by fluorescence spectrometry. The reaction was excited at 366 nanometers and produced fluorescence at 515 nanometers. Additional experimental results suggest that the fluorescence did not arise from the buffer.

EXAMPLE 9

Preparation of Fluorescent Gold Nanoclusters Using Chitosan Template

Several aqueous solutions of Chitosan (SIGMA) and HAuCl$_4$ were prepared. Some of the solutions were prepared by adding Chitosan (1% by weight) to nanopure water (1 mL, pH 3-4 adjusted with acetic acid). Others were prepared by adding Chitosan to PBS (1 M, pH=7.2). An amount of HAuCl$_4$ at a Chitosan to gold ratio of 1:5 was mixed in. The solutions were incubated for 24 hours at different temperatures (37 degrees Celsius, 42 degrees Celsius, and 56 degrees Celsius). After the incubation period, a pink colored solution was obtained for both PBS and nanopure water solution, without black precipitates, at a reaction temperature above 42 degrees Celsius. A colorless solution without any precipitate was obtained at 37 degrees Celsius. The solutions were then examined using fluorescence spectroscopy. For each of the reactions, an excitation/emission maxima of 305/395 nm was observed, but with different emission intensity. The PBS-containing solution at 56 degree Celsius produced a more intense fluorescence, which was due to the presence of gold nanoclusters of different sizes. The PBS solution at 56 degrees Celsius produced the highest intensity. The fluorescence is due to the presence of gold nanoclusters of different sizes. Additional experimental results suggest that the fluorescence did not arise from the Chitosan.

EXAMPLE 10

Stability of Fluorescent Au$_8$ Nanoclusters as a Function of pH

In order to determine whether gold nanoclusters produced according to this invention would be suitable for tagging biomolecules in a living cell, the effect of pH on monodisperse gold nanoclusters was examined. A sample of monodisperse, G4OH dendrimer-enclosed nanoclusters of a formula believed to be Au$_8$ was prepared. Samples of dendrimer-enclosed nanoclusters prepared at 37 degrees Celsius from solutions with and without ascorbic acid were compared (all other parameters were the same). Samples that showed no further increase in fluorescence intensity (i.e. samples at equilibrium) were divided into four aliquots, each with a pH of around 6. The pH of the four aliquots was adjusted to pH 2-3, pH 4-5, pH 7-8 and pH 9-10, and the fluorescence intensities of the aliquots were monitored over time at room temperature. At pH 2-3, the fluorescence intensity dropped significantly after 72 hours, indicating the unstable nature of these nanoclusters in acidic solution. The gold nanoclusters are relatively stable at pH 4-5 for up to two days at room temperature but prolonged exposure at pH 4-5 leads to eventual decrease in fluorescence intensity. Nearly no change in fluorescence intensity was observed for the solution at pH 7-8. At a pH value of pH 9-10, a drop of the fluorescence intensity was observed, but not as significant a drop as what was observed in acidic solution, indicating that gold nanoclusters are generally more stable in a basic solution than in an acidic solution. Cellular fluids generally have a pH in a range of from about 6.9 to about 7.4, and the above results indicate that these gold nanoclusters are stable enough in this cellular pH range to be used for bio-labeling.

EXAMPLE 11

Preparation of Gold Nanoclusters in Nonaqueous Media

Dendrimer encapsulated gold nanoclusters were synthesized using hydroxyl-terminated ethylenediamine core dendrimers in nonaqueous solvents (methanol or toluene). In this EXAMPLE, a solution of $AuPMe_3Cl$ (3.2 μmol, 1.0 mg) in methanol (3.24 mL) was prepared. A portion of this solution (280 microliters, 0.28 micromoles, 4 equiv of $AuPMe_3Cl$) and G4OH dendrimer (10 microliters, 0.07 micromoles) were co-dissolved in methanol (1 mL), and the resulting mixture was stirred vigorously for two days at room temperature, during which time the solution remained colorless. Afterward, the solution was transferred to a glass vial (2 mL). The vial was capped and heated to a temperature of about 75 degrees Celsius with stirring for about 30 hours (a control run using the same composition but without the gold solution was also performed). The reaction was monitored by fluorescence spectroscopy and the product was a monodisperse $Au_8$, according to the Jellium model. While a temperature of about 37 degrees Celsius was sufficient for reduction of gold chloride, a higher temperature was necessary for reduction of gold phosphite. The use of phosphine-stabilized gold precursor prevents nanoparticle formation, thus improves the reaction yield.

EXAMPLE 12

Preparation of an Aqueous Solution of Gold Nanoclusters from a Nonaqueous Solution The as-prepared nanoclusters of EXAMPLE 11 were dried out from methanol and resuspended into water. A solution of gold nanoclusters in methanol (1 mL) was dried using a flow of nitrogen gas. The solid residue was dissolved in water (1 mL). The fluorescence of the gold nanoclusters in water was only slightly less than that in methanol solution. The ability to prepare this gold nanocluster in aqueous solution facilitates their use as molecular probes in biological systems.

EXAMPLE 13

Synthesis of Polypeptide CCCCGSSRDE (SEQ ID NO: 1)

This polypeptide was synthesized by solid phase peptide synthesis using standard Fmoc chemistry, The Fmoc group was de-protected by piperidine in NMP. The polypeptide was cleaved from the resin using 95% TFA in the presence of $H_2O$, triisopropylsilane, thioanisole, anisole, and DTT. During this process, the side protection groups were also de-protected. The polypeptide was precipitated in ethyl ether and lyophilized. The crude product was used without further purification.

EXAMPLE 14

Preparation of Gold Nanoclusters Using Polypeptide Template CCCCGSSRDE (SEQ ID NO: 1)

An aqueous solution was prepared by adding the polypeptide CCCCGSSRDE (SEQ ID NO: 1) (1 mg, 0.94 μmol) to nanopure water (1 mL), and then mixing in $HAuCl_4$ where the ratio of polypeptide to $HAuCl_4$ was 1:2. The pH of the solution was adjusted to pH 3-4 using 1 M acetic acid. The solution was then cooled on ice for 2 hours. Excess cold sodium borohydride solution was then added to the mixture on ice. The solution was then buffered back to pH 6-7 and stirred at degrees Celsius for 24 hours. A turbid, light yellow solution was obtained. After centrifugation, colorless supernatant and yellow precipices, which can be readily dispersed in tris buffer, were obtained. The solution, supernatant and precipitates were then examined using fluorescence. When excited at 450 nm, the solution mixture had a broad emission around 640 nm; the supernatant had an emission maximum at 530 nm; and the precipitates had an emission at 730 nm. The fluorescence is due to the presence of gold nanoclusters or gold sulfate complex.

EXAMPLE 15

Preparation of Gold Nanoclusters Using Polypeptide Template CCCCGSSRDE (SEQ ID NO: 1) in a Buffered Solution An aqueous buffered solution was prepared by adding the polypeptide CCCCGSSRDE (SEQ ID NO: 1) (1 mg, 0.94 μmol) with to Phosphate Buffered Saline solution (1 mL, PBS), and then mixing in $HAuCl_4$ where the ratio of polypeptide to $HAuCl_4$ was 1:2. The solution was then cooled on ice for 2 hours. Excess cold sodium borohydride solution was then added to the mixture on ice. The solution was then buffered back to pH 6-7 and stirred at degrees Celsius for 24 hours. A turbid, light yellow solution was obtained. After centrifugation, colorless supernatant and yellow precipices, which can be readily dispersed in tris buffer, were obtained. The solution, supernatant and precipitates were then examined using fluorescence. When excited at 450 nm, the solution mixture had a broad emission around 640 nm; the supernatant had an emission maximum at 530 nm; and the precipitates had an emission at 730 nm. The fluorescence is due to the presence of gold nanoclusters or gold sulfate complex.

EXAMPLE 16

Preparation of Silver Nanoclusters Using the Polypeptide Template CCCCGSSRDE (SEQ ID NO: 1)

A cold, aqueous solution of the cysteine rich polypeptide CCCCGSSRDE (SEQ ID NO: 1) and silver precursor was used to form nanoclusters as follows: a solution was prepared by adding the embodiment polypeptide CCCCGSSRDE (SEQ ID NO: 1) (1 mg 0.94 μmol) to nanopure water (1 mL)

and then mixing in an amount of AgNO$_3$ (0.0092M, aqueous solution, ALDRICH). The ratio of peptide to AgNO$_3$ was 1:2. The pH of the solution was adjusted to 3-4 using 1 M acetic acid. The solution was then cooled on ice for 2 hours. Excess cold sodium borohydride solution was then added to the mixture on ice. The solution was then buffered back to 6-7 and stirred at degrees Celsius for 24 hour. A turbid, light yellow solution was obtained. After centrifugation, colorless supernatant and yellow precipices, which can be readily dispersed in tris buffer, were obtained. The solution, supernatant and precipitates were then examined using fluorescence. When excited at 450 nm, the solution mixture and the precipitates both have emissions at 725 nm; and no evident emission was seen from the supernatant. Further UV-radiation decrease the intensity of emission and shift the emission maximum to higher wavelength. The fluorescence is due to the presence of silver nanoclusters or silver sulfate complex.

EXAMPLE 17

Preparation of Silver Nanoclusters Using the Polypeptide Template CCCCGSSRDE in a Buffered Solution A cold, aqueous solution of the cysteine rich polypeptide CCCCGSSRDE and silver precursor was used to form nanoclusters as follows: a solution was prepared by adding the embodiment polypeptide CCCCGSSRDE (1 mg, 0.94 µmol) to PBS solution (1 mL) and then mixing in an amount of AgNO$_3$ (0.0092M, aqueous solution, ALDRICH). The ratio is of peptide to AgNO$_3$ was 1:2. The solution was then cooled on ice for 2 hours. Excess cold sodium borohydride solution was then added to the mixture on ice. The solution was then buffered back to 6-7 and stirred at degrees Celsius for 24 hour. A turbid, light yellow solution was obtained. After centrifugation, colorless supernatant and yellow precipices, which can be readily dispersed in tris buffer, were obtained. The solution, supernatant and precipitates were then examined using fluorescence. When excited at 450 nm, the solution mixture and the precipitates both have emissions at 725 nm; and no evident emission was seen from the supernatant. Further UV-radiation decrease the intensity of emission and shift the emission maximum to higher wavelength. The fluorescence is due to the presence of silver nanoclusters or silver sulfate complex.

EXAMPLE 19

Preparation of Gold Nanoclusters Using Phage Display

A phage (i.e. bacteriophage) display cycle of selections was completed utilizing two different polypeptide libraries on M13 filamentous phage. Each member of the library is referred to herein as a polypeptide-carrying phage. One of the libraries included polypeptides having 10 amino acids. The second library included polypeptides having 12 amino acids. Briefly, these libraries were contacted with gold plated glass slides. Polypeptide-carrying phages from these libraries that did not bind to the gold plated slide were washed away. Polypeptide-carrying phages that bound with the gold were eluted, and later amplified. The process was continued for two more times. The polypeptide-carrying phages that bound to the gold plated glass slides were then screened individually to determine which were suitable for the production of fluorescent gold nanoclusters by mixing them with HAuCl$_4$ in Phosphate Buffered Saline solution (1 M, pH=7.2) and turning the resulting solution in an incubator for seven days at 37 degrees Celsius. Fluorescence spectrometry was used to determine which of the individual polypeptide-carrying phages formed nanoclusters. The DNA of these polypeptide-carrying phages was sequenced, the amino acid sequence connectivity of the polypeptide for these phages was determined, and the polypeptides were chemically synthesized. Embodiment polypeptides selected by phage display that are useful for preparing noble metal nanoclusters included PHDARGRSAG (SEQ ID NO: 2), SDSYIHARPR (SEQ ID NO: 3), PLVERLYPRL (SEQ ID NO: 4), TGRDTKTGTS (SEQ ID NO: 5), RPTNAGKMTN (SEQ ID NO: 6), VAPWPPLTRK (SEQ ID NO: 7), MAPTPPLTRK (SEQ ID NO: 8), RWAPMSCLVT (SEQ ID NO: 9), YLEFPRRGYLLP (SEQ ID NO: 10), ASSPHDARGRSAG (SEQ ID NO: 11), ASSSDSYIHARPR (SEQ ID NO: 12), ASSPLVERLYPRL (SEQ ID NO: 13), ASSTGRDTKTGTS (SEQ ID NO: 14), ASSRPTNAGKMTN (SEQ ID NO: 15), ASSVAPWPPLTRK (SEQ ID NO: 16), ASSMAPTPPLTRK (SEQ ID NO: 17), ASSRWAPMSCLVT (SEQ ID NO: 18), and ASSYLEFPRRGYLLP (SEQ ID NO: 19).

In summary, the invention is concerned with the preparation of fluorescent metal nanoclusters using dendrimers, polypeptides, proteins, or small molecules as templates. Polypeptide templates that enclose and protect the nanoclusters may allow them to be attached to a biomolecule.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preparing fluorescent nanoclusters, comprising:
mixing an aqueous solution of a dendrimer template and a metal precursor in a dark environment at a temperature of 4 degrees Celsius that is cold enough to prevent the substantial formation of non-fluorescent metal nanoclusters and nanoparticles but allow the formation of a complex between the dendrimer template and metal from the metal precursor, whereby a complex forms between the template and metal from the metal precursor; and increasing the temperature, whereby the complex is reduced and fluorescent metal nanoclusters are produced.

2. The method of claim 1, wherein the metal precursor comprises gold or silver.

3. The method of claim 1, wherein the nanoclusters have a size less than 1 nanometer.

4. The method of claim 1, wherein the metal precursor is chosen from $AuPR_3X$, $HAuX_4$, and $AgClO_4$, wherein R is chosen from alkyl and aryl, and wherein X is selected from fluoride, chloride, bromide, and iodide.

5. The method of claim 1, wherein the template is a dendrimer.

6. The method of claim 1, wherein the template is a hydroxyl-terminated dendrimer or a carboxyl-terminated dendrimer.

7. The method of claim 6, wherein the hydroxyl-terminated or carboxyl terminated dendrimer comprises poly(amidoamine), poly(amidoethylenediamine), DAB-Am-16, polypropylenimine hexadecaamine dendrimer, or cyclotriphosphazene-PMMH-24 dendrimer.

8. The method of claim 1, wherein the aqueous solution further comprises a biocompatible reducing agent.

9. The method of claim 1, wherein the nanoclusters are monodisperse.

10. The method of claim 8, wherein the monodisperse nanoclusters are of the formula $Au_8$ or $Au_{11}$.

11. The method of claim 1, further comprising separating the gold nanoclusters from the template.

12. The method of claim 9, further comprising separating the monodisperse gold nanoclusters from the template and thereafter attaching the monodisperse nanoclusters to a biomolecule.

13. The method of claim 1, wherein the fluorescent nanoclusters are formed on a solid support, wherein the solid support comprises a spherical surface or a planar surface.

14. A method of preparing fluorescent metal nanoclusters, comprising:
mixing a two-phase liquid system comprising an aqueous phase and an organic phase, the aqueous portion comprising a biocompatible reducing agent and a dendrimer template, the organic portion comprising metal precursor, the metal chosen from gold and silver;
separating the aqueous phase from the organic phase after mixing the two-phase liquid system; and
heating the aqueous solution, thereby preparing fluorescent metal nanoclusters.

15. The method of claim 14, further comprising the step of separating the template from the nanoclusters.

16. The method of claim 14, wherein the nanoclusters have a size less than 1 nanometer.

17. The method of claim 1, wherein the step of increasing the temperature is increasing the temperature to 37 degrees Celsius.

18. A method for preparing fluorescent nanoclusters, comprising:
mixing an aqueous solution of a dendrimer template and a metal precursor in a dark environment at a temperature of 4 degrees Celsius that is cold enough to prevent the substantial formation of non-fluorescent metal nanoclusters and nanoparticles but allow the formation of a complex between the dendrimer template and metal from the metal precursor, whereby a complex forms between the template and metal from the metal precursor; and without adding any additional reducing agent capable of reducing the complex formed between the dendrimer template and the metal from the metal precursor,
increasing the temperature, whereby the complex is reduced and fluorescent metal nanoclusters are produced.

19. The method of claim 18, wherein the metal nanoclusters are gold nanoclusters.

20. The method of claim 19, wherein the gold nanoclusters are $Au_8$ nanoclusters.

* * * * *